US012653407B2

(12) United States Patent　　　　(10) Patent No.:　US 12,653,407 B2
Tsai et al.　　　　　　　　　　　　(45) Date of Patent:　　Jun. 16, 2026

(54) APPARATUS AND METHOD FOR HEART RATE MEASUREMENT

(71) Applicant: Artilux, Inc., Menlo Park, CA (US)

(72) Inventors: Jui-Wei Tsai, Hsinchu County (TW); Chun-Wei Chang, Hsinchu County (TW); Chieh Yin, Hsinchu County (TW); Kai-Wei Chiu, Hsinchu County (TW)

(73) Assignee: Artilux, Inc., Menlo Park, CA (US)

( * ) Notice: Subject to any disclaimer, the term of this patent is extended or adjusted under 35 U.S.C. 154(b) by 64 days.

(21) Appl. No.: 18/743,844

(22) Filed: Jun. 14, 2024

(65) Prior Publication Data

US 2024/0407658 A1　　Dec. 12, 2024

Related U.S. Application Data

(63) Continuation-in-part of application No. 18/456,488, filed on Aug. 26, 2023, now Pat. No. 12,551,122.

(60) Provisional application No. 63/382,112, filed on Nov. 3, 2022.

(51) Int. Cl.
*A61B 5/024*　　　(2006.01)
*A61B 5/00*　　　(2006.01)

(52) U.S. Cl.
CPC ...... *A61B 5/02416* (2013.01); *A61B 5/02438* (2013.01); *A61B 5/721* (2013.01); *A61B 5/7214* (2013.01)

(58) Field of Classification Search
None
See application file for complete search history.

(56) References Cited

U.S. PATENT DOCUMENTS

| | | | |
|---|---|---|---|
| 2017/0128020 A1* | 5/2017 | Olivier | A61B 5/721 |
| 2019/0192079 A1* | 6/2019 | Groenendaal | A61B 5/02433 |
| 2020/0178821 A1* | 6/2020 | Wu | A61B 5/721 |
| 2021/0093211 A1 | 4/2021 | Gbati I | |
| 2022/0192515 A1* | 6/2022 | Yeo | A61B 5/7207 |
| 2023/0010538 A1 | 1/2023 | Klamkin | |
| 2023/0081794 A1 | 3/2023 | Mäkinen et al. | |
| 2023/0107454 A1* | 4/2023 | Similä | A61B 5/681 |
| | | | 600/479 |
| 2023/0397847 A1 | 12/2023 | Wengarten | |
| 2024/0049970 A1 | 2/2024 | Matsumura et al. | |
| 2024/0081696 A1 | 3/2024 | De Benedetto et al. | |

* cited by examiner

*Primary Examiner* — Patricia J Park

(74) *Attorney, Agent, or Firm* — Dority & Manning, P.A.

(57)　　　　ABSTRACT

A method for obtaining a heart rate value by an optical sensing apparatus includes: receiving, by a first calculator in a processor and from a light receiver, a PPG signal; receiving, by a second calculator in the processor and from a motion sensor, a motion signal; determining, by the first calculator, a first heart rate value; determining, by the first calculator, a validity indicator according to the PPG signal; and determining, by the second calculator, a second heart rate value according to the PPG signal and the motion signal. When the validity indicator is determined to satisfy a predetermined requirement, the processor outputs the first heart rate value as the heart rate value. When the validity indicator is determined to not satisfy the predetermined requirement, the processor outputs the second heart rate value as the heart rate value.

20 Claims, 15 Drawing Sheets

100

500

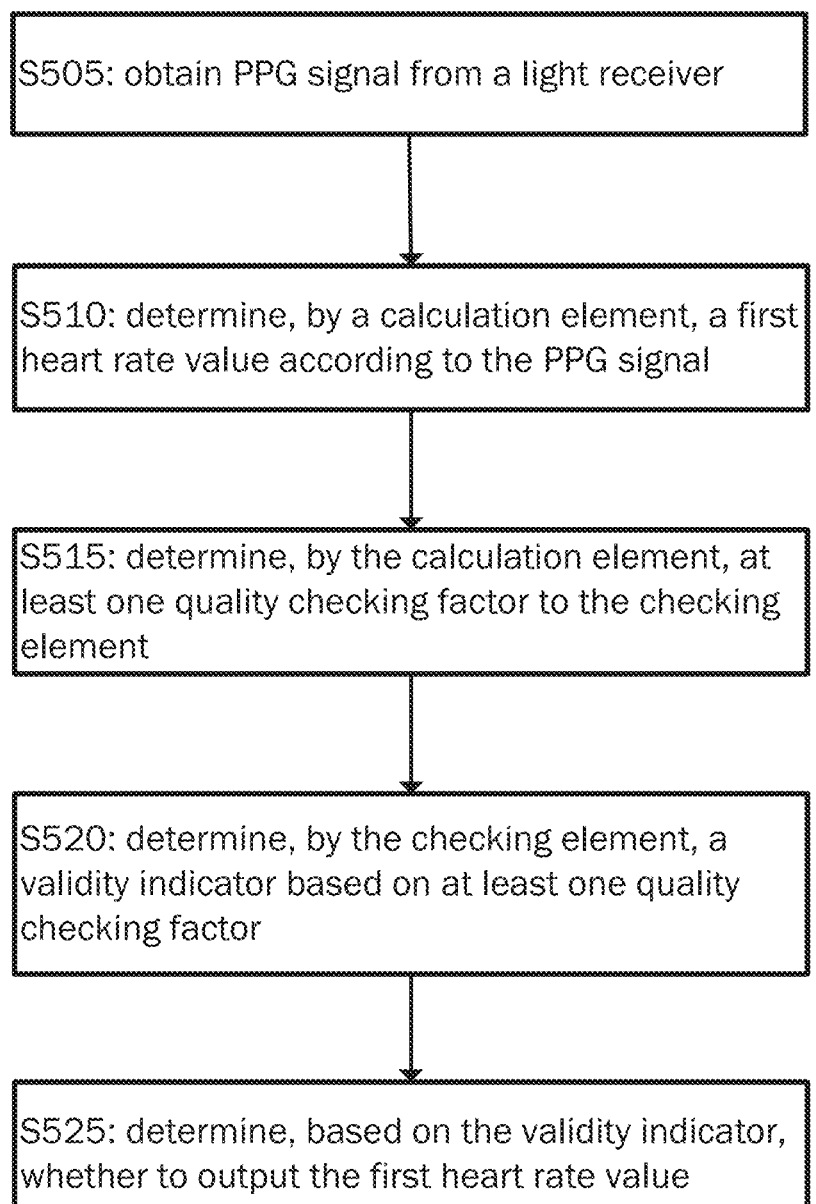

S505: obtain PPG signal from a light receiver

S510: determine, by a calculation element, a first heart rate value according to the PPG signal S515: determine, by the calculation element, at least one quality checking factor to the checking element S520: determine, by the checking element, a validity indicator based on at least one quality checking factor S525: determine, based on the validity indicator, whether to output the first heart rate value

FIG. 5A

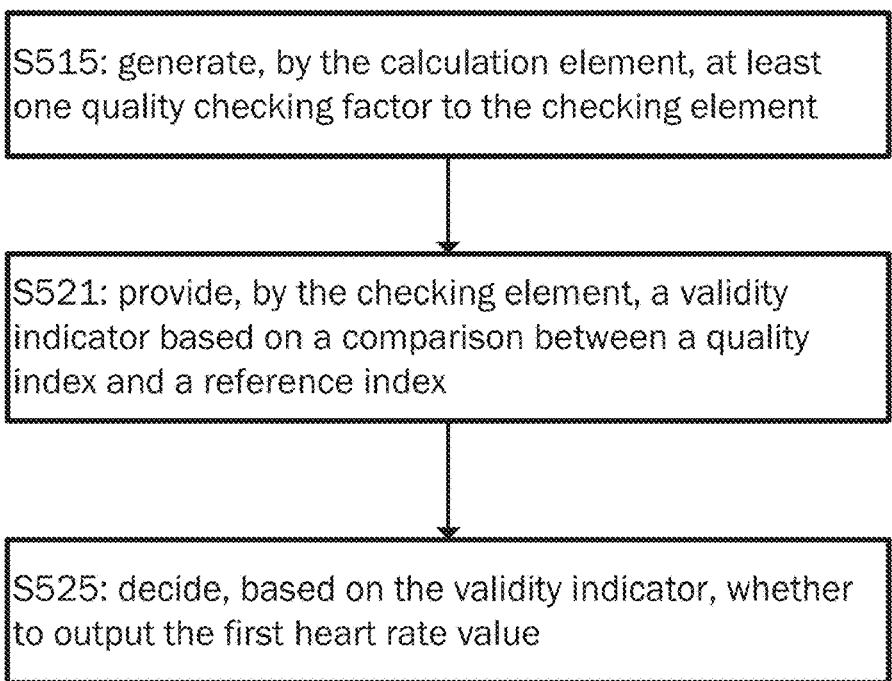

S515: generate, by the calculation element, at least one quality checking factor to the checking element S521: provide, by the checking element, a validity indicator based on a comparison between a quality index and a reference index S525: decide, based on the validity indicator, whether to output the first heart rate value

FIG. 5B

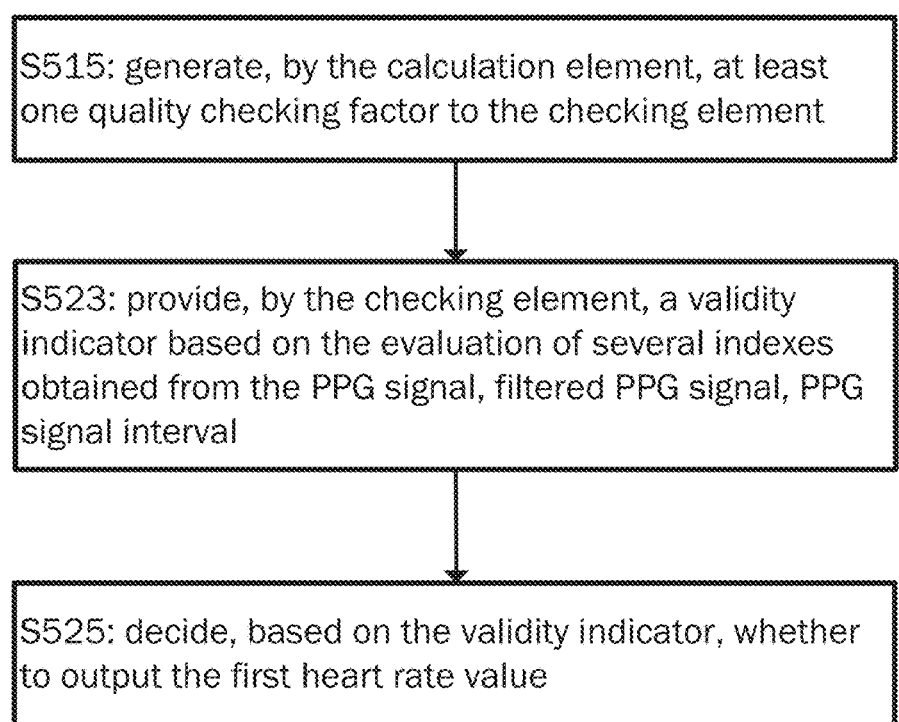

S515: generate, by the calculation element, at least one quality checking factor to the checking element S523: provide, by the checking element, a validity indicator based on the evaluation of several indexes obtained from the PPG signal, filtered PPG signal, PPG signal interval S525: decide, based on the validity indicator, whether to output the first heart rate value

FIG. 5C

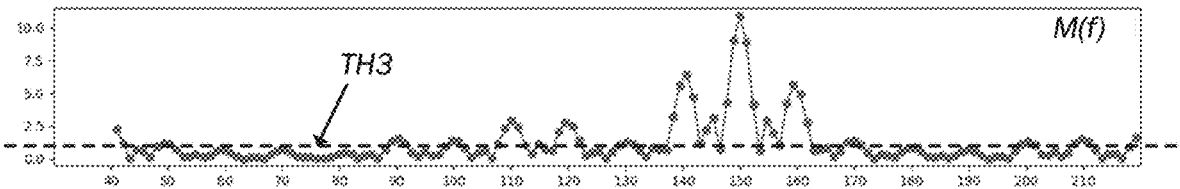
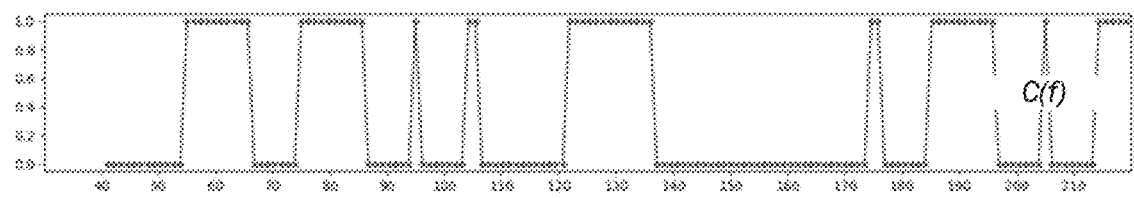
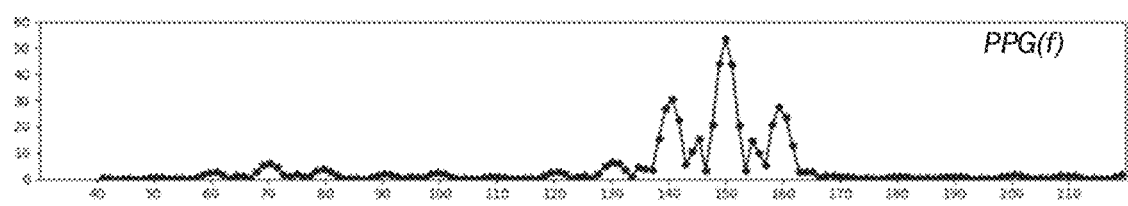
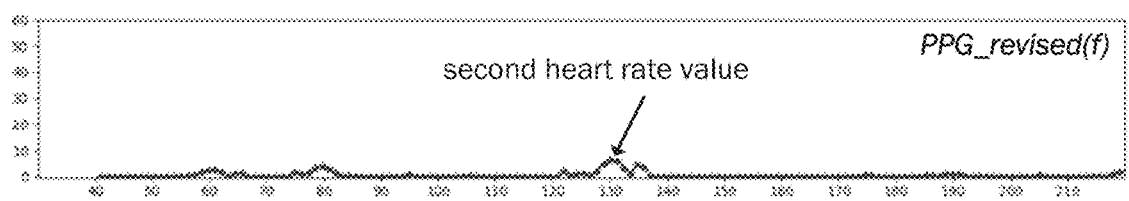
FIG.6B

700

700

700

APPARATUS AND METHOD FOR HEART RATE MEASUREMENT

CROSS-REFERENCE TO RELATED APPLICATIONS

This present application is a continuation-in-part of U.S. Non-Provisional patent application Ser. No. 18/456,488 filed on Aug. 26, 2023, which claims priority to U.S. Provisional Patent Application No. 63/382,112, filed Nov. 3, 2022. Applicant claims priority to and the benefit of each of such applications and incorporates all such applications herein by reference in its entirety.

FIELD

The present application is related to heart rate measurement technology. In particular, methods and apparatuses (e.g., optical sensing apparatuses) are disclosed for obtaining a heart rate value.

BACKGROUND

Optical sensors are being used in many systems, such as smartphones, wearable electronics, robotics, and autonomous vehicles, etc. for proximity detection, 2D/3D imaging, object recognition, image enhancement, material recognition, color fusion, health monitoring, and other relevant applications.

SUMMARY OF THE INVENTION

The present disclosure concerns an electronic device having an optical sensing apparatus, where the electronic device can calculate the heart rate by a processor, thereby the bioinformation from the heart rate can be continuously monitored with low power consumption. The optical sensing apparatus can be operable for different wavelength ranges, including visible (e.g., wavelength range 380 nm to 780 nm, or a similar wavelength range as defined by a particular application) and non-visible light. The non-visible light includes near-infrared (NIR, e.g., wavelength range from 780 nm to 1400 nm, or a similar wavelength range as defined by a particular application) and short-wavelength infrared (SWIR, e.g., wavelength range from 1400 nm to 3000 nm, or a similar wavelength range as defined by a particular application) light.

One aspect of the present disclosure is directed to an apparatus including a processor configured to calculate heart rate information. The processor includes a heart rate calculator including a memory configured to store a PPG signal and a calculation element coupled to the memory and configured to calculate a heart rate value and generate at least one quality checking factor according to the PPG signal.

The processor also includes a checking element configured to determine a validity indicator according to the at least one quality checking factor, a memory control element coupled to the memory and configured to access the memory to transmit the PPG signal, and a multiplexer configured to output the PPG signal accessed by the memory control element or the heart rate value calculated by the calculation element according to the validity indicator.

In some implementations, the calculation element includes an analysis circuit configured to calculate the heart rate value by detecting peaks of the PPG signal and calculating an interval between peaks.

In some implementations, the calculation element includes a matched filter configured to determine a quality index representing the at least one quality checking factor.

In some implementations, the quality index is determined by calculating a mean absolute value of the PPG signal.

In some implementations, the calculation element includes a DC subtraction element configured to receive the PPG signal and to output an AC signal having a DC value removed from the PPG signal and a band-pass filter configured to receive the AC signal and to output a band-passed signal having out-of-band signals removed from the AC signal.

In some implementations, the processor includes a skin detector configured to detect the presence of an object's skin.

In some implementations, the processor includes a controller configured to operate the skin detector and the heart rate calculator in an interleaving manner.

In some implementations, the apparatus includes a light receiver including one or more photodetectors and a control device including the processor.

In some implementations, the one or more photodetectors are formed on a first substrate wafer-bonded to the control device formed on a second substrate.

In some implementations, a bonding interface exists between the one or more photodetectors and the processor.

In some implementations, the one or more photodetectors are stacked on the control device.

In some implementations, the processor includes a controller configured to control the light receiver.

In some implementations, the one or more photodetectors include a plurality of sensing areas deposited on a substrate, the plurality of sensing areas being composed of a material different from the substrate.

In some implementations, the memory control element is configured to output the PPG signal in a first-in-first-out (FIFO) configuration.

Another aspect of the present disclosure is directed to a method of heart rate calculation performed by an apparatus including a processor. The method includes obtaining a PPG signal from a light receiver arranged in the apparatus, calculating, by a calculation element arranged in the processor, a heart rate value according to the PPG signal, and generating, by the calculation element, at least one quality checking factor to a checking element arranged in the processor. The method also includes providing, by the checking element, a validity indicator based on the at least one quality checking factor, and determining whether to output the heart rate value based on the validity indicator.

In some implementations, the method includes determining whether to output the PPG signal based on the validity indicator.

In some implementations, the method includes detecting peaks of the PPG signal and calculating the interval between peaks to calculate the heart rate value.

In some implementations, the method includes obtaining a mean absolute value by a matched filter to generate a quality index to be the at least one quality checking factor.

In some implementations, the method includes storing the PPG signal in a memory.

In some implementations, the heart rate value is obtained every one computation cycle of the PPG signal.

Another aspect of the present disclosure is directed to a method for obtaining a heart rate value by an optical sensing apparatus. The method includes receiving, by a first calculator in a processor and from a light receiver, a PPG signal. The method also includes receiving, by a second calculator in the processor and from a motion sensor, a motion signal. The method also includes determining, by the first calculator in the processor, a first heart rate value. The method also includes determining, by the first calculator in the processor, a validity indicator according to the PPG signal. The method also includes determining, by the first calculator in the processor, whether the validity indicator satisfies a predetermined requirement. The method also includes outputting, by the processor, the first heart rate value as the heart rate value, when the validity indicator satisfies the predetermined requirement. The method also includes determining, by the second calculator in the processor, a second heart rate value according to the PPG signal and the motion signal, when the validity indicator does not satisfy the predetermined requirement. The method also includes outputting, by the processor, the second heart rate value as the heart rate value, when the validity indicator does not satisfy the predetermined requirement.

In some implementations, the determining step of the second heart rate value by the second calculator includes: receiving, by the second calculator and from the first calculator, the PPG signal; transforming, by the second calculator, the motion signal into a motion spectrum; transforming, by the second calculator, the PPG signal into a PPG spectrum; determining, by the second calculator, a motion cancellation parameter by comparing the motion spectrum with a predetermined threshold; determining, by the second calculator, a revised PPG spectrum by revising the PPG spectrum by the motion cancellation parameter; and determining, by the second calculator, the second heart rate value by detecting a peak frequency of the revised PPG spectrum.

In some implementations, the determining step of the motion cancellation parameter includes: when the motion spectrum at a first frequency is not less than the predetermined threshold, the motion cancellation parameter is a first value at the first frequency; and when the motion spectrum at a second frequency is less than the predetermined threshold, the motion cancellation parameter is a second value at the second frequency.

In some implementations, the first value is 0 and the second value is 1.

In some implementations, the method also includes setting the motion cancellation parameter to the second value at a specific frequency within an estimated heart rate range.

In some implementations, the revised PPG spectrum is derived by multiplying the PPG spectrum by the motion cancellation parameter.

In some implementations, the motion sensor is implemented by an optical detector operating at a different wavelength than the light receiver.

In some implementations, the method also includes: receiving, by the first calculator in the processor and from the motion sensor, the motion signal; and determining, by the first calculator in the processor, a validity indicator according to analysis of the PPG signal and analysis of the motion signal.

In some implementations, the method also includes: receiving, by a PPG evaluator in a processor and from a light receiver, the PPG signal; classifying, by the PPG evaluator in the processor, the PPG signal and determining a classification information; and outputting, by the PPG evaluator in the processor, an evaluation result based on the classification information.

In some implementations, the light receiver and the motion sensor are implemented by a single light receiver.

Another aspect of the present disclosure is directed to an optical sensing apparatus configured to obtain a heart rate value. The apparatus includes a motion sensor, a light receiver, and a processor including a first calculator and a second calculator. The processor is configured to receive, by the first calculator and from the light receiver, a PPG signal. The processor is also configured to receive, by the second calculator and from the motion sensor, a motion signal. The processor is also configured to determine, by the first calculator, a first heart rate value. The processor is also configured to determine, by the first calculator, a validity indicator according to the PPG signal. The processor is also configured to determine, by the first calculator, whether the validity indicator satisfies a predetermined requirement. The processor is also configured to output, by the processor, the first heart rate value as the heart rate value, when the validity indicator satisfies the predetermined requirement. The processor is also configured to determine, by the second calculator, a second heart rate value according to the PPG signal and the motion signal, when the validity indicator does not satisfy the predetermined requirement. The processor is also configured to output, by the processor, the second heart rate value as the heart rate value, when the validity indicator does not satisfy the predetermined requirement.

In some implementations, the motion sensor is implemented by an optical detector operating at a different wavelength than the light receiver.

In some implementations, the light receiver and the motion sensor are implemented by a single light receiver.

In some implementations, the second calculator is configured to: receive, from the first calculator, the PPG signal; transform, the motion signal into a motion spectrum; transform, the PPG signal into a PPG spectrum; determine, a motion cancellation parameter by comparing the motion spectrum with a predetermined threshold; determine, a revised PPG spectrum by revising the PPG spectrum by the motion cancellation parameter; and determine, the second heart rate value by detecting a peak frequency of the revised PPG spectrum.

In some implementations, when the motion spectrum at a first frequency is not less than the predetermined threshold, the motion cancellation parameter is a first value at the first frequency; and when the motion spectrum at a second frequency is less than the predetermined threshold, the motion cancellation parameter is a second value at the second frequency.

In some implementations, the revised PPG spectrum is derived by multiplying the PPG spectrum by the motion cancellation parameter.

Another aspect of the present disclosure is directed to a method for obtaining a heart rate value by an optical sensing apparatus. The method includes receiving, by a processor and from a light receiver, a PPG signal. The method also includes receiving, by the processor and from a motion sensor, a motion signal. The method also includes transforming, by the processor, the motion signal into a motion spectrum. The method also includes transforming, by the processor, the PPG signal into a PPG spectrum. The method also includes determining, by the processor, a motion cancellation parameter by comparing the motion spectrum with a predetermined threshold. The method also includes determining, by the processor, a revised PPG spectrum by revising the PPG spectrum by the motion cancellation parameter. The method also includes determining, by the processor, the heart rate value by detecting a peak frequency of the revised PPG spectrum.

In some implementations, when the motion spectrum at a first frequency is not less than the predetermined threshold, the motion cancellation parameter is a first value at the first frequency; and when the motion spectrum at a second frequency is less than the predetermined threshold, the motion cancellation parameter is a second value at the second frequency.

In some implementations, the method also includes setting the motion cancellation parameter to the second value at a specific frequency within an estimated heart rate range.

In some implementations, the revised PPG spectrum is derived by multiplying the PPG spectrum by the motion cancellation parameter.

BRIEF DESCRIPTION OF THE DRAWINGS

The foregoing aspects and many of the advantages of this application will become more readily appreciated as the same becomes better understood by reference to the following detailed description, when taken in conjunction with the accompanying drawings:

FIG. 5A illustrates a calculation flow of the first calculator of the heart rate calculator in accordance with one embodiment of the present disclosure.

FIG. 5B illustrates a calculation flow of the first calculator of the heart rate calculator in accordance with another embodiment of the present disclosure.

FIG. 5C illustrates a calculation flow of the first calculator of the heart rate calculator in accordance with another embodiment of the present disclosure.

FIG. 6B illustrates signal spectrum diagrams processed in the second calculator in accordance with one embodiment of the present disclosure.

DETAILED DESCRIPTION

Figure 1A:
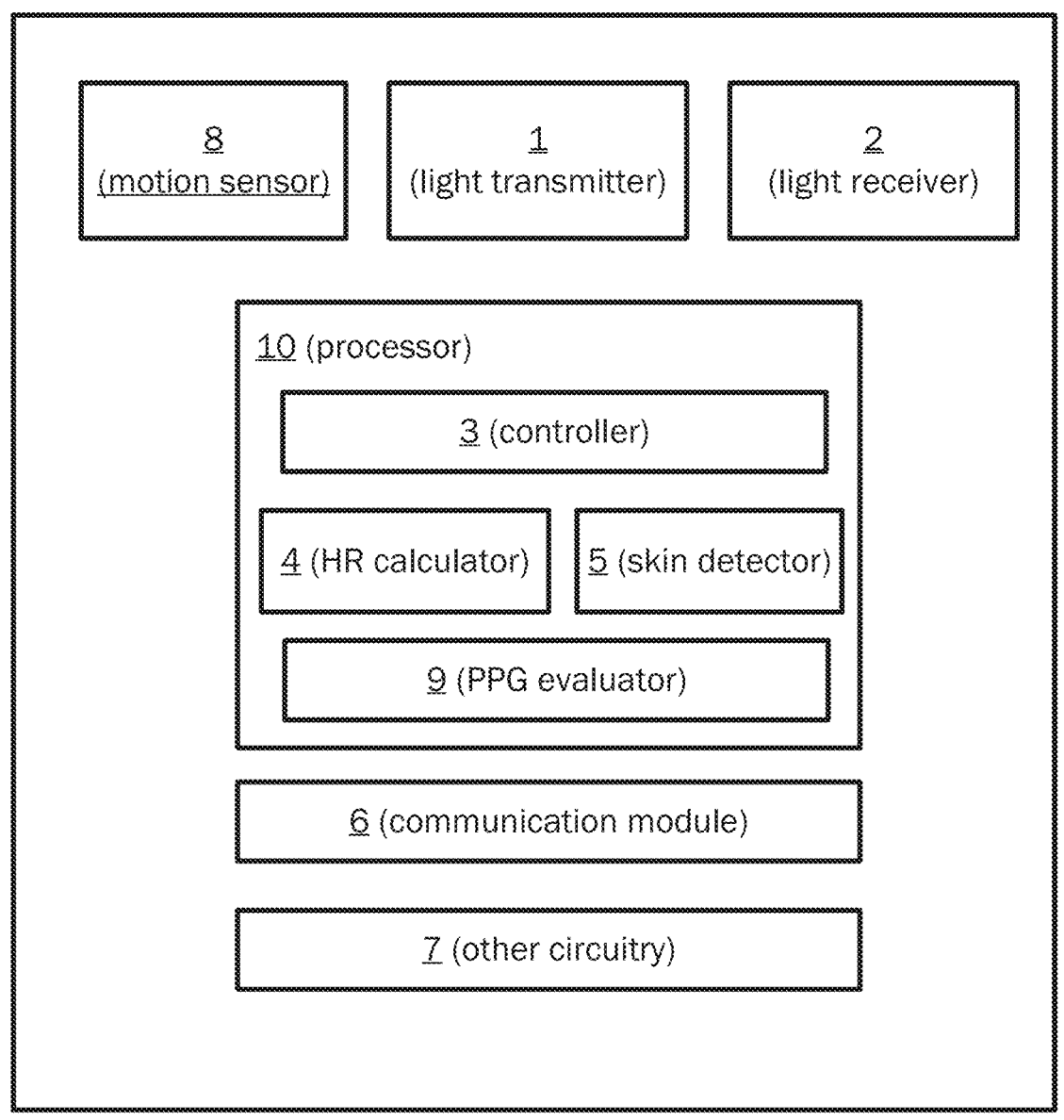
FIG. 1A illustrates a block diagram of an optical sensing apparatus in accordance with one embodiment of the present disclosure.

The following embodiments accompany the drawings to illustrate the concept of the present disclosure. In the drawings or descriptions, similar or identical parts use the same reference numerals, and in the drawings, the shape, thickness, or height of the element can be reasonably expanded or reduced. The embodiments listed in the present application are only used to illustrate the present application and are not used to limit the scope of the present application. Any obvious modification or change made to the present application does not depart from the spirit and scope of the present application.

In general, wearable electronic devices (e.g., earbuds, AR/VR wearable equipment, wristband, etc.) can be worn on a user for various activities, such as playing music, exercise, athletic training, rest, daily life activities, physical therapy, etc. The electronic device with a personal health monitor function can provide users with bioinformation during activities. For example, a photoplethysmogram (PPG) is an optically obtained plethysmogram, which can be used to determine various bioinformation such as heart rate, calories, skin moisture, blood oxygen level ($SpO_2$), and/or blood pressure, etc. In some cases, the bioinformation is calculated by the software of the electronic device, which consumes a lot of power during the calculation, so that the electronic device cannot be used for a long time without charging. In addition, the speed of software calculation may be slower than that of hardware calculation, and the calculation process by software may potentially slow down other software running on the electronic device. Thus, an electronic device that can provide accurate bioinformation and reduce power consumption is still an important issue. In this way, the user can wear the electronic device for a long time without frequent charging. Moreover, this disclosure describes an optical sensing apparatus that can either calculate heart rates using hardware or software depending on the signal quality of the PPG signal, which can provide more reliable measurements based on different operating conditions.

FIG. 1A illustrates a block diagram of an optical sensing apparatus 100 in accordance with one embodiment of the present disclosure. The optical sensing apparatus 100 can be located in an electronic device (not shown) which can be a wearable device or a portable device. The wearable device can be an earbud, a wristband, a wristwatch, a pair of glasses, a helmet, a head-mounted device, or other wearable electronic device. The portable device can be a cellular telephone, tablet computer, laptop computer, computer mouse, computer stylus, or other accessories. The optical sensing apparatus 100 can include a light transmitter 1, a light receiver 2, a motion sensor 8, a processor 10, a communication module 6, and other circuitries 7.

The light transmitter 1 can include one or more light sources which can emit light with the same wavelength or different wavelengths for object detection, bioinformation measurement, and/or indication. In an embodiment, the light transmitter 1 may include a first light source that can emit a NIR light and a second light source that can emit a SWIR light. In another embodiment, multiple light sources can emit SWIR lights. Light transmitted by the light transmitter 1 may be absorbed and/or reflected by an object that is in proximity to the electronic device (not shown). The light receiver 2 is configured to detect the reflected light from the object that is in proximity to the electronic device. The light receiver 2 may include one or more photodetectors to receive light corresponding to the lights emitted from the light transmitter 1 for object detection and/or bioinformation measurement. The bioinformation measurement can be calculated by the processor 10 according to the sensing signal from the light receiver 2, such as the PPG signal. In some embodiments, one or more photodetectors of the light receiver 2 may include a photodetector for three-dimensional (3D) depth sensing (e.g., i-TOF or d-TOF photodetector), proximity sensing, optical spectroscopy, two-dimensional (2D) sensing (e.g., 2D IR imaging), or a combination thereof. Each of the photodetectors can be implemented using a single photodetector or an array of photodetector pixels (e.g., 1D or 2D photodetector array as described in reference to FIGS. 8 and 9).

The motion sensor 8 is configured to output a motion signal in response to the user's movement. The bioinformation, such as heart rate value, calculated by the processor based on the sensing signal from the light receiver 2 can be easily interfered with by the wearing condition or the user's movement. For example, activities like jogging, climbing stairs, cycling, etc. can interfere with the sensing signal, making it difficult for the processor to obtain accurate bioinformation. The motion sensor can output the user's movement information to the processor, and the processor can use the output from the motion sensor to eliminate interference from the user's movement on the sensing signal to obtain accurate bio-information. The motion sensor can include, but is not limited to, an accelerometer, an optical detector, a CCD camera, a piezoelectric sensor, or any type of sensor capable of detecting motion information. In one embodiment, the motion sensor is implemented by an optical detector for receiving signals at different wavelengths than the optical receiver. For example, the optical detector is configured to receive a first signal with a strong PPG signal at a first wavelength, and the optical detector used for the motion sensor 8 is configured to receive a second signal with a weak PPG signal at a second wavelength. The second wavelength may be greater than the first wavelength, for example, the first wavelength is approximately 1050 nm and the second wavelength is approximately 1450 nm. In one embodiment, the light receiver 2 and the optical detector used for the motion sensor 8 can be implemented by a single broadband or multi-band light receiver, so that the size of the optical sensing apparatus 100 can be reduced.

The processor 10 can be implemented by digital processor (DSP), general purpose processor, application-specific integrated circuit (ASIC), digital circuitry, or any combinations thereof. The processor 10 can include a controller 3, a heart rate (HR) calculator 4, a skin detector 5, and a PPG evaluator 9. The controller 3 is configured to control the light transmitter 1 and the light receiver 2. The heart rate calculator 4 is configured to receive at least one of the PPG signals from the light receiver 2 and the motion signals from the motion sensor 8 to calculate a heart rate value. The skin detector 5 is configured to detect the presence of the object's skin. As an example, if the user has not properly worn the electronic device, the skin detector 5 cannot recognize the presence of the object and the heart rate calculator 4 will not operate to calculate the heart rate value for saving the power consumption. In an embodiment, the skin detector 5 and the heart rate calculator 4 operate in an interleaving manner (e.g., alternating measurements in time) for precisely monitoring the bioinformation. The PPG evaluator 9 is configured to evaluate the quality of the PPG signal and transmit the evaluation results to the user wearing the optical sensing module through the communication module 6. The user can adjust the wearing position according to the evaluation results output by the PPG evaluator 9 to obtain a PPG signal with better signal quality for other bioinformation sensing calculations. The communication module 6 is configured to transmit and receive electrical signals from the processor 10 to one or more other devices, and vice versa, via one or more communications protocols (e.g., WiFi, BLUETOOTH, cellular). The other circuitries 7 can be any other circuitries (e.g., charging circuitry, additional processing circuitry, memory, other sensors) equipped on the optical sensing apparatus 100.

Figure 1B:
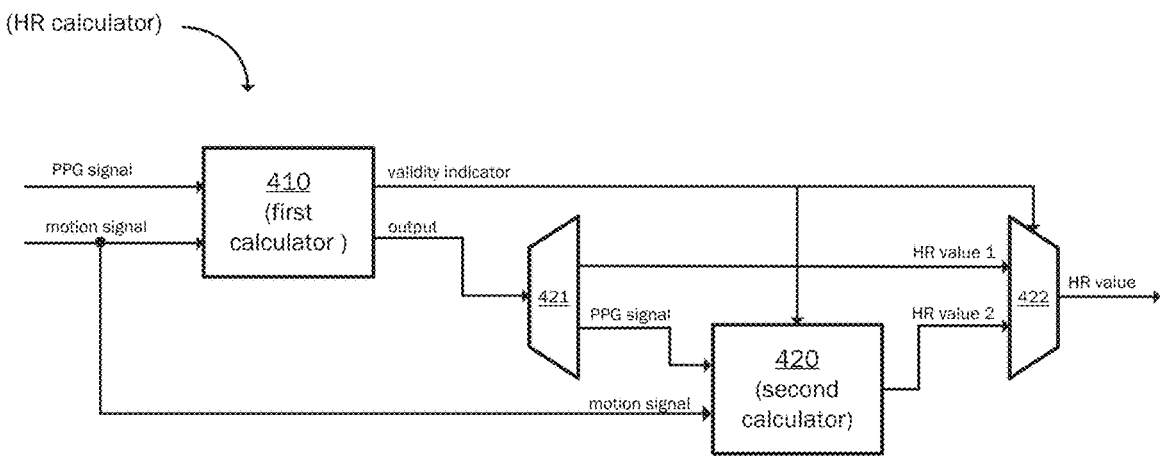
FIG. 1B illustrates a block diagram of a heart rate calculator of the processor in accordance with one embodiment of the present disclosure.

FIG. 1B illustrates a block diagram of a heart rate calculator 4 of the processor in accordance with one embodiment of the present disclosure. The heart rate calculator 4 may include a first calculator 410 for determining the first heart rate value (HR value 1) through a first method and a second calculator 420 for determining the second heart rate value (HR value 2) through a second method. The first calculator 410 can receive the PPG signal from the light receiver 2 and provide an output and a validity indicator representing the signal quality of the PPG signal. The first calculator 410 may also optionally receive the motion signal from the motion sensor as an input signal for generating the validity indicator. The output of the first calculator 410 may include at least one of the first heart rate value (HR value 1) determined by the first method and the PPG signal. When the validity indicator indicates that the signal quality of the PPG signal is not good, the output of the first calculator 410 may include the PPG signal and the second calculator may receive the output from the first calculator 410 to determine the second heart rate value. Then, the heart rate calculator 4 may output the second heart rate value as the heart rate value. On the contrary, when the validity indicator indicates that the signal quality of the PPG signal is good enough, the output of the first calculator 410 may include the first heart rate value determined by the first calculator 410, which can be the output of the heart rate calculator 4 as the heart rate value. In an implementation, the first calculator 410 transmits the output to the second calculator 420 through a demultiplexer 421. The heart rate calculator 4 may include a multiplexer 422 for receiving the output from the first calculator 410 and the output from the second calculator to output one of the first heart rate value and the second heart rate value as the heart rate value according to the validity indicator. In another implementation, any of the demultiplexer 421 and the multiplexer 422 may be replaced by a selector or a switch.

The second calculator 420 receives the output including the PPG signal from the first calculator 410 and the motion signal from the motion sensor, and determines a second heart rate value (HR value 2). In an implementation, the second calculator 420 can be controlled to receive the output from the first calculator 410 by the validity indicator. When the validity indicator indicates that the signal quality of the PPG signal is not good, the second calculator 420 is controlled to receive the output of the first calculator 410.

Figure 1C:
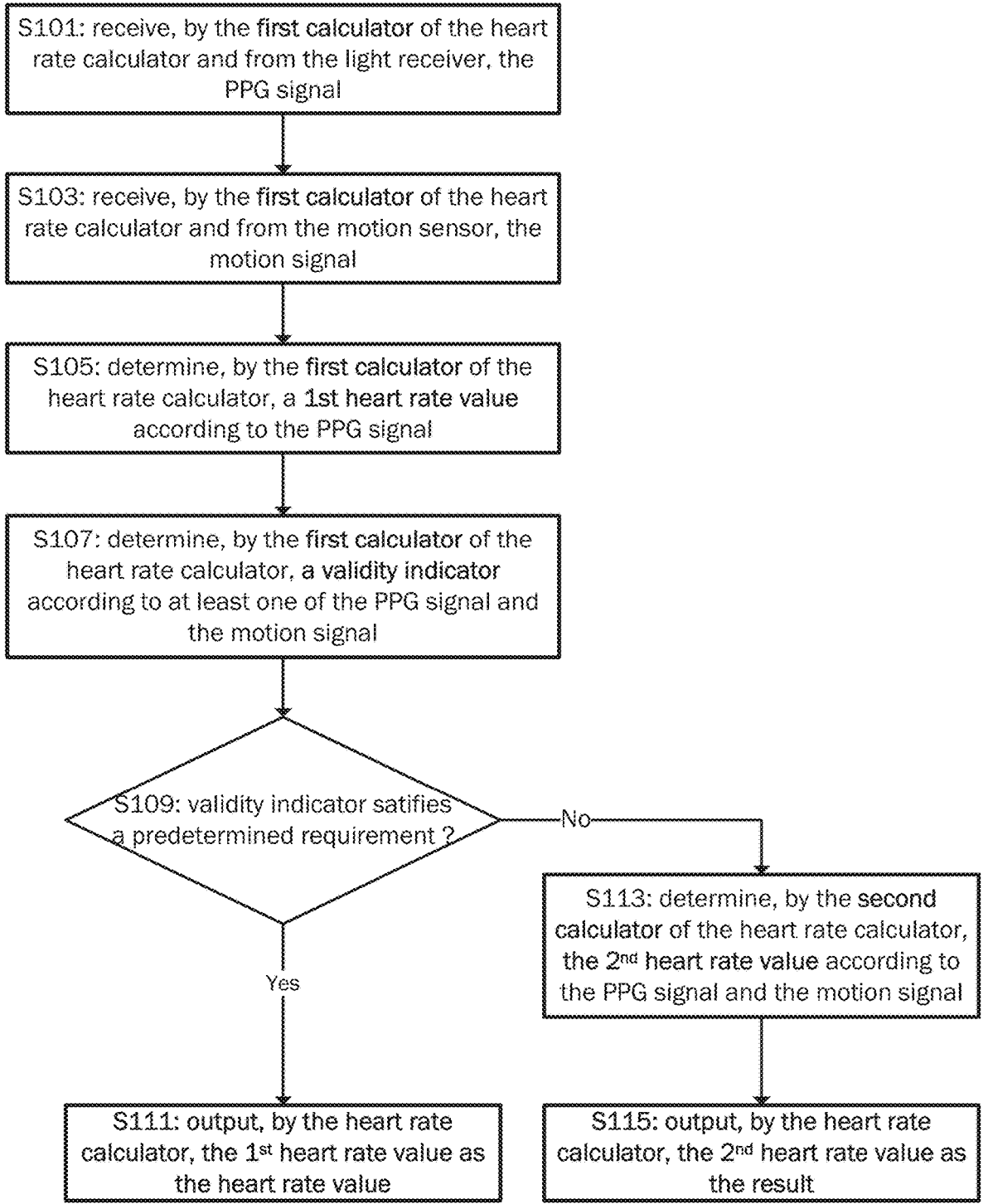
FIG. 1C illustrates a heart rate calculation flow of the heart rate calculator in accordance with one embodiment of the present disclosure.

FIG. 1C illustrates a heart rate calculation flow of the heart rate calculator 4 in accordance with one embodiment of the present disclosure. In step S101, the first calculator of the heart rate calculator 4 may receive the PPG signal from the light receiver. In step S103, the first calculator of the heart rate calculator 4 may receive the motion signal from the motion sensor. In step S105, the first calculator of the heart rate calculator 4 determines the first heart rate value (HR value 1) according to the PPG signal. In step S107, the first calculator of the heart rate calculator 4 determines a validity indicator according to at least one of the PPG signal and the motion signal. In step S109, the first calculator of the heart rate calculator 4 determines whether the validity indicator satisfies a predetermined requirement. The heart rate calculator 4 can obtain the signal quality of the PPG signal according to the validity indicator to decide to output the heart rate value determined by the first calculator or the second calculator. In step S111, when the validity indicator satisfies the predetermined requirement, it means that the signal quality of the PPG signal is good enough and the PPG signal is not interfered by the user's movement. Therefore, the heart rate calculator 4 can output the first heart rate value obtained from the first calculator according to the PPG signal as the heart rate value. In step S113, when the validity indicator does not satisfy the predetermined requirement, it means that the signal quality of the PPG signal is not good and the PPG signal may be interfered with by the user's movement. The first calculator of the heart rate calculator 4 outputs the PPG signal to the second calculator, and the second calculator receives the PPG signal from the first calculator and the motion signal from the motion sensor to determine the second heart rate value. Subsequently, the second calculator of the heart rate calculator 4 determines the second heart rate value (HR value 2) according to the PPG signal and the motion signal. Then, in step S115, the heart rate calculator 4 can output the second heart rate value obtained from the second calculator as the heart rate value.

The heart rate calculator 4 can flexibly choose to utilize the first calculator 410 or the second calculator 420 to obtain the heart rate value based on the signal quality of the PPG signal. Since the first calculator 410 only needs to analyze and process the PPG signal to determine the first heart rate value, it may use fewer computing resources of the processor to obtain the heart rate value. Thereby achieving the advantage of saving power consumption, and can also obtain the heart rate value more quickly and immediately. When the signal quality of the PPG signal is poor due to interference from the user's movement, the interfered PPG signal contains the motion signal. The second calculator 420 can obtain the motion signal from the motion sensor and remove the interference of the motion signal from the PPG signal to obtain a more accurate heart rate value.

Figure 1D:
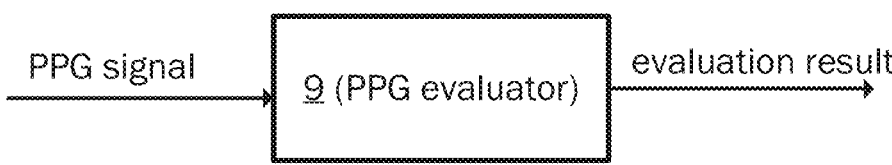
FIG. 1D illustrates a block diagram of a PPG evaluator of the processor in accordance with one embodiment of the present disclosure.

FIG. 1D illustrates a block diagram of a PPG evaluator of the processor in accordance with one embodiment of the present disclosure. The PPG evaluator 9 can receive the PPG signal from the light receiver 2 and provide at least one evaluation result representing the signal quality of the PPG signal. The PPG evaluator 9 is configured to classify the received PPG signals. The PPG evaluator 9 can identify the relationship between the waveform of the PPG signal and the wearing position of the optical sensing apparatus, and output the classification of the PPG signal relating to the wearing position as the evaluation result. The optical sensing apparatus 100 can output the evaluation result to the user (not shown) through the communication module 6. The user can adjust the wearing position according to the evaluation result so that the optical sensing apparatus 100 can obtain a better-quality PPG signal. In one embodiment, the PPG evaluator 9 can include at least one machine-learning model (e.g., a heuristic-based model, a deep learning model, a regression-based model) to analyze the waveform of the PPG signal and provide the classification related to the wearing position. For example, an optical sensing apparatus is installed in an earbud. Through the evaluation results of the PPG evaluator, the user can be notified that the earbud needs to be turned left or right when wearing it so that the optical sensing apparatus can obtain a better-quality PPG signal. In another example, the user can be notified that the earbud has become loose in the ear and needs to be re-worn to obtain a better-quality PPG signal based on the evaluation results.

Figure 1E:
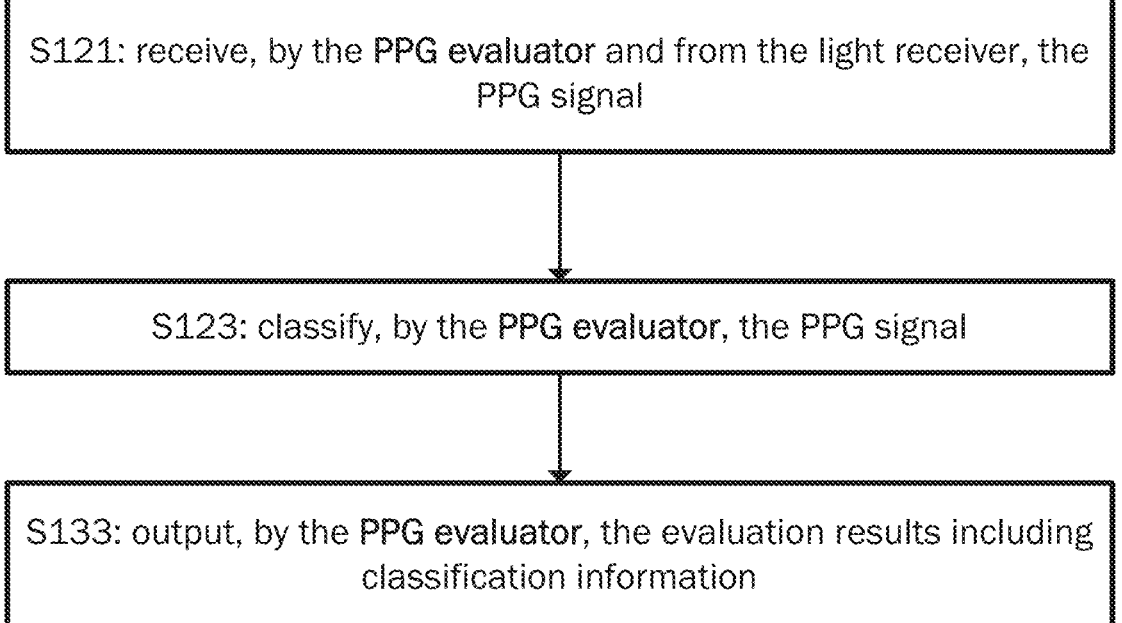
FIG. 1E illustrates a PPG evaluation flow in accordance with one embodiment of the present disclosure.

FIG. 1E illustrates a PPG evaluation flow in accordance with one embodiment of the present disclosure. In step S121, the PPG evaluator of the processor can receive the PPG signal from the light receiver. In step S123, the PPG evaluator of the processor can classify the PPG signal. In one implementation, the PPG evaluator classifies the PPG signal based on the waveform of the PPG signal through a machine-learning model. In step S125, the PPG evaluator of the processor can output the evaluation results including classification information. In one implementation, the PPG evaluator can output the evaluation results to the user through the communication module, and the user can adjust the wearing position of the optical sensing apparatus based on the evaluation results.

In one embodiment, during initial calculation, the heart rate calculator or other calculators that use PPG signals to calculate bioinformation (e.g., calories, blood oxygen level (SpO$_2$), and/or blood pressure) may require a longer time (e.g., several seconds) to sample multiple PPG signals to obtain the calculation result for initial calculation. The PPG evaluator can be activated during the initial calculation so that subsequent heart rate calculations or other bioinformation calculations can obtain more accurate results. In another embodiment, the PPG evaluator can be activated periodically to maintain a better wearing position of the optical sensing apparatus.

Figure 2A:
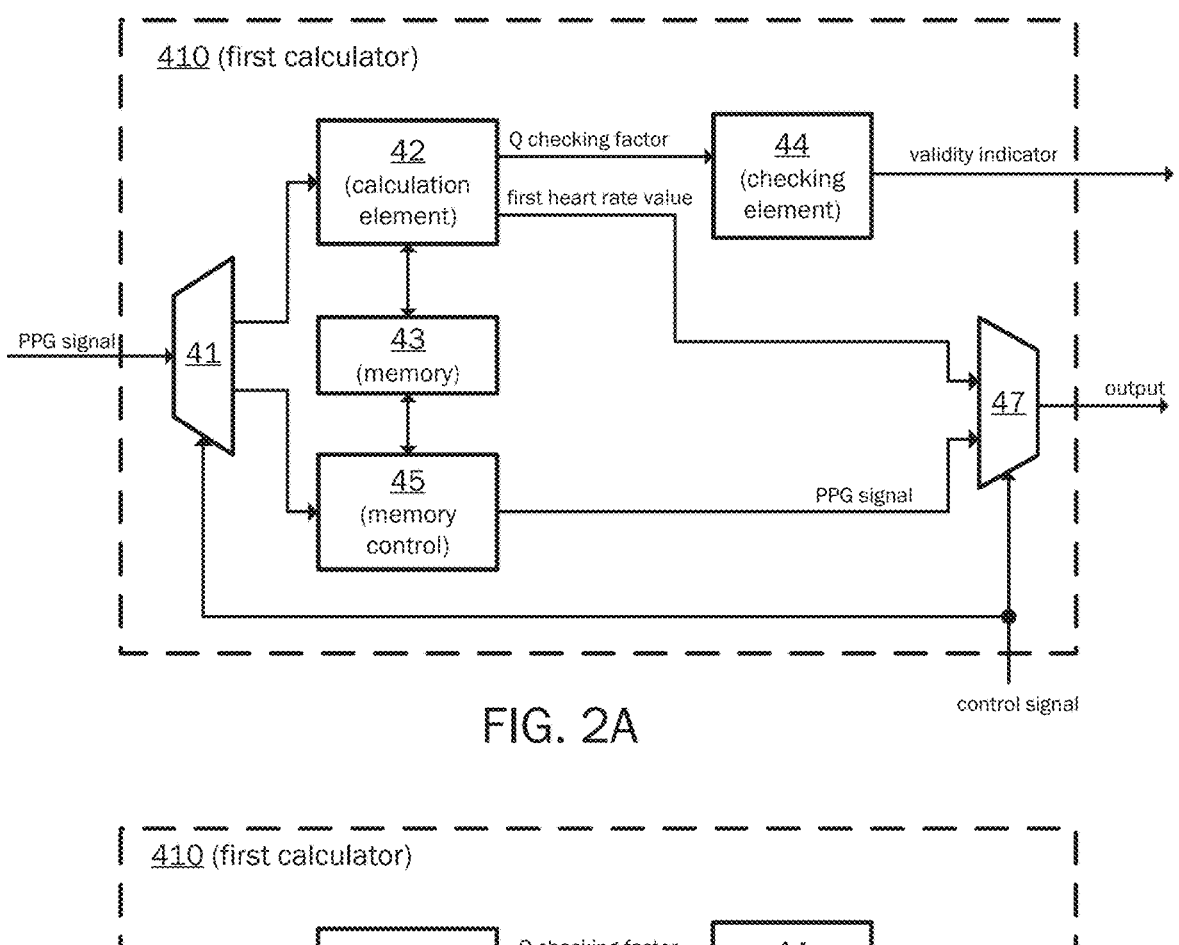
FIG. 2A illustrates a block diagram of a first calculator of the heart rate calculator of the optical sensing apparatus in accordance with one embodiment of the present disclosure.

FIG. 2A illustrates a block diagram of a first calculator 410 of the heart rate calculator 4 of the optical sensing apparatus 100 in accordance with one embodiment of the present disclosure. The first calculator 410 is configured to receive the sensing signals from the light receiver 2 and provides an output and a validity indicator to the electronic device or other computing devices, such as smartphone, watch, or computer, and/or other processing units for further signal processing or identification. The first calculator 410 is used to provide the first heart rate value when the signal quality of the PPG signal is good enough. When the signal quality of the PPG signal is not good, the first calculator 410 may be configured to transmit the PPG signal instead. In other words, the first calculator 410 can output the first heart rate value or the PPG signal to the electronic device and/or other processing units based on the validity indicator. The validity indicator can represent the signal quality of the PPG signal.

The first calculator 410 includes a calculation element 42, a memory 43, a checking element 44, a memory control element 45 (e.g., FIFO), a demultiplexer 41, and multiplexer 47. When the skin detector 5 as shown in FIG. 1 recognizes the presence of the object's skin, the first calculator 410 receives the PPG signal from the light receiver 2, which is transmitted to the calculation element 42 through the demultiplexer 41 and stored in the memory 43. The calculation element 42 is configured to calculate the first heart rate value by detecting the peaks of the PPG signal and calculating the interval of the peaks of the PPG signal. Furthermore, the calculation element 42 can output at least one quality checking factor (Q checking factor). The checking element 44 is configured to receive at least one quality checking factor from the calculation element 42 and determine a validity indicator to indicate the signal quality of the PPG signal. If the validity indicator shows valid for the PPG signal, a control signal is sent to the multiplexer 47 to control the first calculator 410 to output the first heart rate value through the multiplexer 47. If the validity indicator shows invalid for the PPG signal, a control signal is sent to the multiplexer 47 and the demultiplexer 41 to control the first calculator 410 to output the PPG signal through the memory control element 45, the memory 43, and the multiplexer 47 for subsequent processing. In another embodiment, when the validity indicator shows valid for the PPG signal and the user has sufficiently accurate heart rate information, a control signal also can be sent to the multiplexer 47 to control the first calculator 410 to output the PPG signal for other bioinformation, such as calories, blood oxygen level (SpO$_2$), and/or blood pressure, etc. The control signal can come from a hardware (e.g., a separate controller) coupled with the validity indicator, an application-level software that is operable to issue a control signal in response to the validity indicator, or a command signal provided by a user.

The memory 43 is configured to store the PPG signal and coupled to the calculation element 42 and the memory control element 45 for providing the PPG signal to the calculation element 42 or the memory control element 45. The PPG signal can be stored in the memory 43 through the calculation element 42 or the memory control element 45. Since the calculation element 42 and the memory control element shares the memory 43, the occupied area of the first calculator 410 can be reduced, and the chip size of the processor 10 can be shrunk.

In an embodiment, when the electronic device or other processing units receives the validity indicator as invalid and the PPG signal from the first calculator 410, the electronic device or other processing units can send the related information to adjust the measurement method, such as adjusting the power of the light transmitter 1, the amplification gain of the light receiver 2, and/or providing a notification to the user to adjust the wearing position of the electronic device.

Figure 2B:
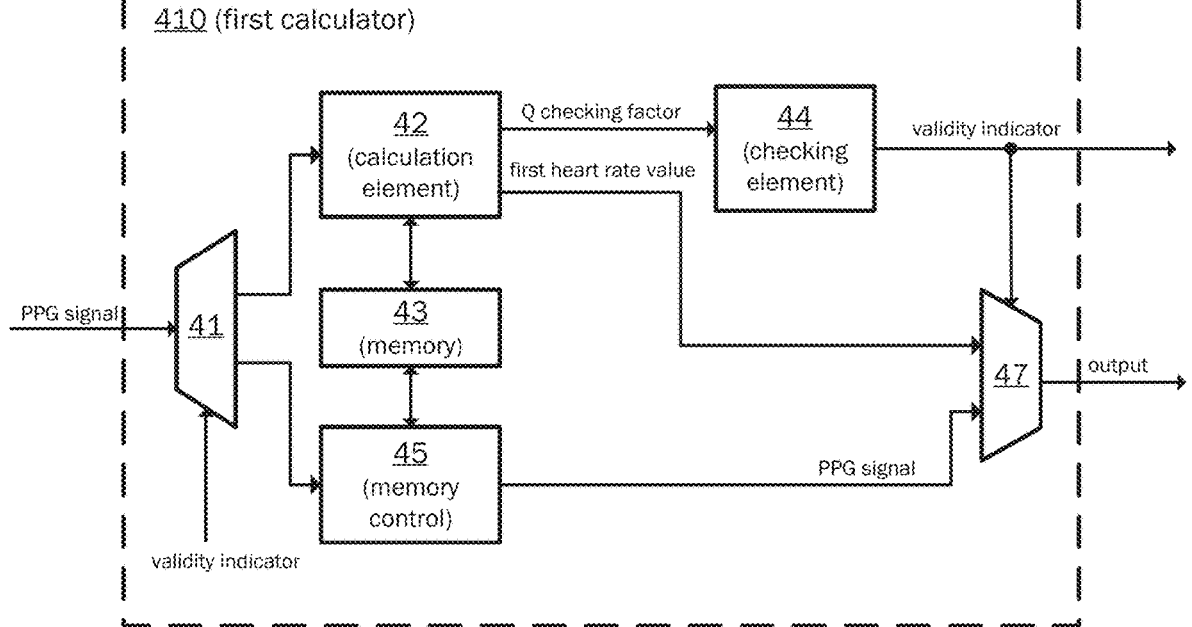
FIG. 2B illustrates a block diagram of a first calculator of the heart rate calculator of the optical sensing apparatus in accordance with another embodiment of the present disclosure.

FIG. 2B illustrates a block diagram of a first calculator 410 of the optical sensing apparatus 100 in accordance with another embodiment of the present disclosure. The first calculator 410 includes a calculation element 42, a memory 43, a checking element 44, a memory control element 45, a demultiplexer 41, and a multiplexer 47. The first calculator 410 can output the first heart rate value or the PPG signal based on the validity indicator. If the validity indicator shows valid, the validity indicator controls the multiplexer 47 and the demultiplexer 41 to cause the first calculator 410 to output the first heart rate value through the multiplexer 47. If the validity indicator shows invalid, the validity indicator controls the multiplexer 47 and the demultiplexer 41 to cause the first calculator 410 to output the PPG signal through the memory control element 45 and the multiplexer 47.

Figure 3A:
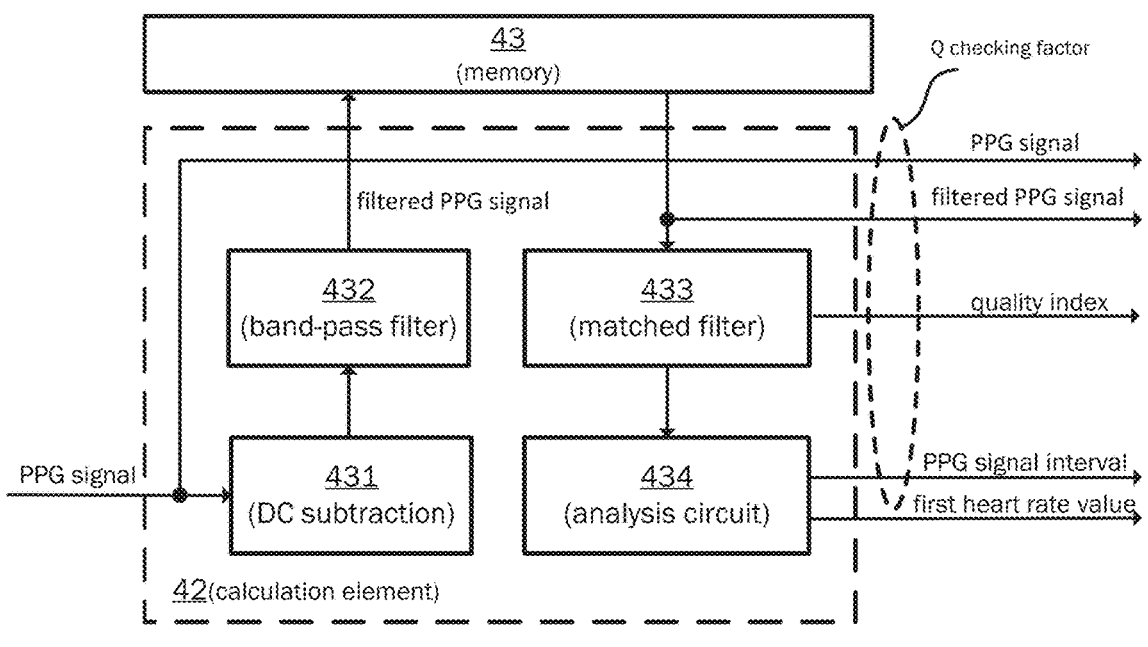
FIG. 3A illustrates a block diagram of a calculation element of the first calculator of the heart rate calculator in accordance with one embodiment of the present disclosure.

FIG. 3A illustrates a block diagram of a calculation element 42 of the first calculator 410 in accordance with one embodiment of the present disclosure. The calculation element 42 is configured to receive the PPG signal to generate at least one Q checking factor and a first heart rate value. At least one Q checking factor can include one or more of PPG signal, filtered PPG signal, quality index, and PPG signal interval. The calculation element 42 includes a DC subtraction element 431, a band-pass filter 432, a matched filter 433, and an analysis circuit 434. The DC subtraction element 431 is configured to receive the PPG signal and to output an AC signal having a DC value removed from the PPG signal. The band-pass filter 432 is configured to receive the AC signal and to output a band-passed signal having out-of-band signals removed from the AC signal. The PPG signal is inputted to the calculation element 42 and processed by the DC subtraction element 431 to remove the DC value of the PPG signal and processed by the band-pass filter 432 to eliminate unwanted out-of-band noises, such as motion artifacts and electromagnetic interferences to obtain a filtered PPG signal with higher signal-to-noise (SNR) ratio. Then, the filtered PPG signal is stored in the memory 43 and can be accessed by the calculation element 42 for subsequent processing. In another embodiment, the PPG signal is inputted to the calculation element 42 and stored in the memory 43 without being processed by the DC subtraction element 431 and the band-pass filter 432. The matched filter 433 is coupled between the memory 43 and the analysis circuit 434 for moving-averaging the periodic PPG signal based on its frequency, and is configured to determine a quality index as one of the Q checking factors. The analysis circuit 434 is coupled to the matched filter 433 to generate the PPG signal interval as one of the Q checking factors and the first heart rate value. The PPG signal interval can be obtained by calculating the interval of the peaks of the PPG signal.

In an embodiment, the quality index is represented as the Q checking factor to transmit to the checking element 44 for validity indicator determination. The matched filter 433 is configured to determine the quality index that represents the signal quality of the PPG signal. In one embodiment, the matched filter 433 is configured to calculate a mean absolute value ($MAV_{PPG}$) of the filtered PPG signal (or PPG signal) which is regarded as the quality index. The matched filter 433 has a plurality of variables (e.g., tap size) to present the ideal PPG profile of the object, and the plurality of variables can be dynamically adjusted with a feedback circuit (not shown) during processing. In addition, the matched filter 433 is also configured to attenuate the unwanted high-frequency noise of the filtered PPG signal (or PPG signal). Therefore, the analysis circuit 434 can receive a low-noise PPG signal from the matched filter 433 for subsequent processing. The analysis circuit 434 is configured to determine the first heart rate value in real-time, e.g. heartbeat, by detecting peaks of the low-noise PPG signal and calculating the interval between peaks.

In an embodiment, referring to FIGS. 2A, 2B, and 3A, the checking element 44 can be configured to compare the quality index (e.g., $MAV_{PPG}$) with a reference index to determine the validity indicator. When the optical sensing apparatus 100 starts up, the light transmitter 1 is inactive and the light receiver 2 is active, a mean absolute value can be obtained through a matched filter which can be located in the calculation element 42 or the checking element 44 to present the background noise ($MAV_{noise}$). The background noise ($MAV_{noise}$) may come from the circuitry of the light receiver 2 or the package of the optical sensing apparatus 100. In an embodiment, the reference index can be set as $C \times MAV_{noise}$, where C is an empirical constant. When the quality index ($MAV_{PPG}$) is greater than the reference index ($C \times MAV_{noise}$), the checking element 44 indicates the validity indicator as valid. Otherwise, the checking element 44 indicates the validity indicator as invalid.

Figure 3B:
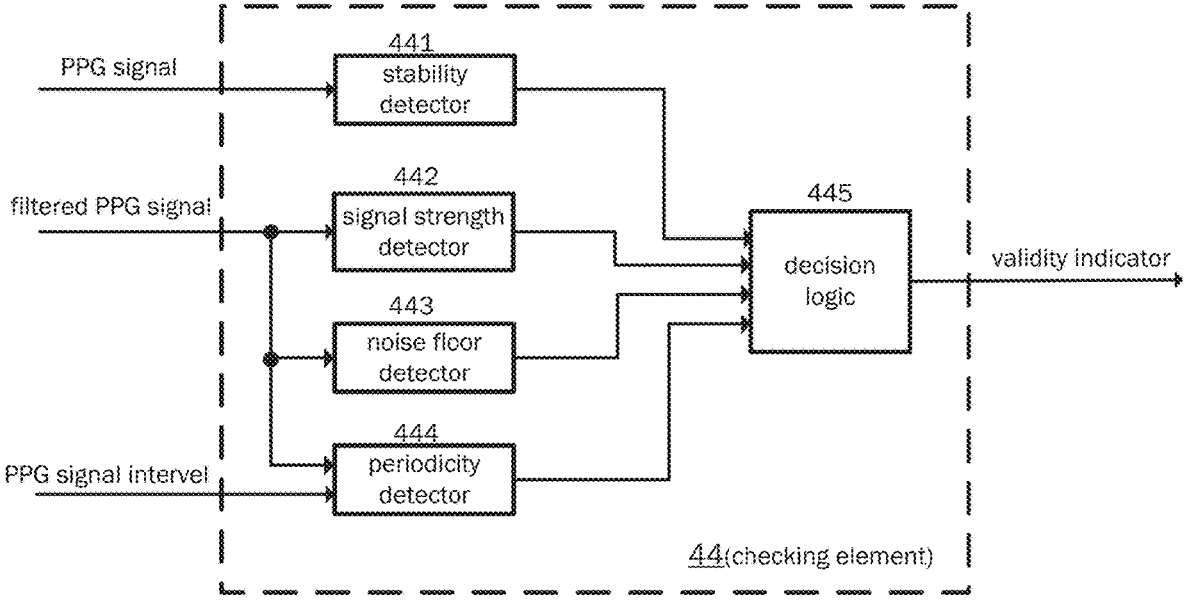
FIG. 3B illustrates a block diagram of a checking element of the first calculator of the heart rate calculator in accordance with one embodiment of the present disclosure.

In another embodiment, PPG signal, filtered PPG signal, and/or PPG signal interval are represented as the Q checking factors to transmit to the checking element 44 for validity indicator determination. FIG. 3B illustrates a block diagram of a checking element 44 of the first calculator 410 in accordance with one embodiment of the present disclosure, where PPG signal, filtered PPG signal, and/or PPG signal interval are represented as Q checking factors. The checking element 44 may include a stability detector 441, a signal strength detector 442, a noise floor detector 443, a periodicity detector 444, and a decision logic 445. The stability detector 441 is configured to detect the stability of the PPG signal and generate a stability index based on the PPG signal. The signal strength detector 442 is configured to detect the signal strength of the PPG signal and generate a signal strength index based on the filtered PPG signal. The noise floor detector 443 is configured to detect the noise floor of the PPG signal and generate the noise floor index from the filtered PPG signal. The periodicity detector 444 is configured to detect the periodicity of the PPG signal and generate a periodicity index from the filtered PPG signal and the PPG signal interval. The decision logic 445 may then determine the validity indicator based on an evaluation of at least one of the stability index, the signal strength index, the noise floor index, and the periodicity index. In an embodiment, each index can be weighted with corresponding weighting values (predetermined or dynamically generated) for evaluation calculation. Each corresponding weighting value may be different or a part of the corresponding weighting values may be different.

In another embodiment, the motion sensor 8 is implemented by an optical detector operating at a different wavelength than the light receiver 2. The checking element 44 may also receive the motion signal from the motion sensor, and utilize at least the signal strength detector 442 and the periodicity detector 444 in the checking element 44 to determine the user's movement information. Then, the decision logic 445 may optionally determine validity indicator based on analysis of motion signals.

The checking element 44 can receive the PPG signal from the light receiver 2 and the motion signal from the motion sensor 8 in a time-division multiplexing manner. The checking element 44 can determine the validity indicator based on the analysis of the PPG signal and the analysis of the motion signal.

Figure 4A:
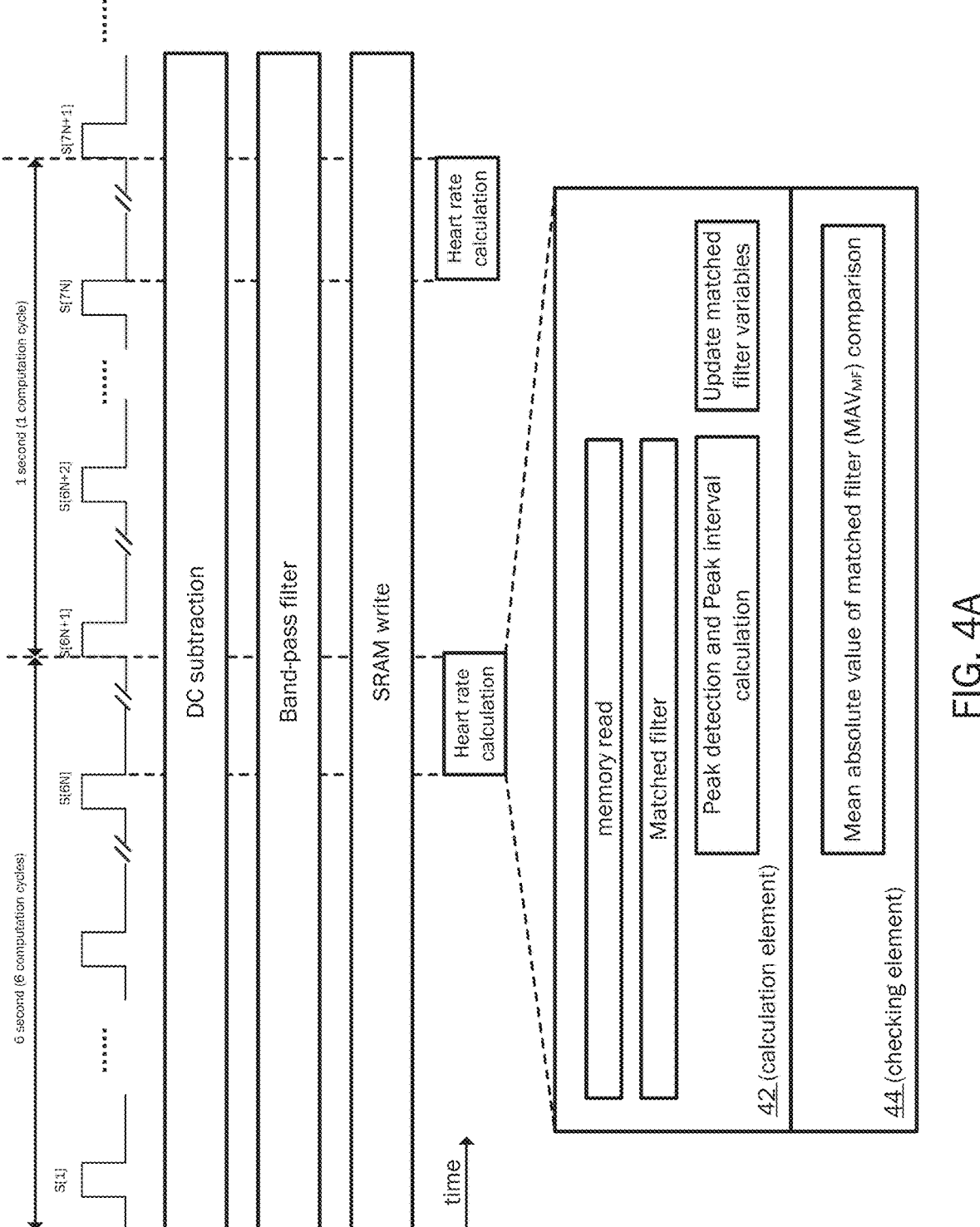
FIG. 4A illustrates a timing sequence of the heart rate calculation of the first calculator in accordance with one embodiment of the present disclosure.
Figure 4B:
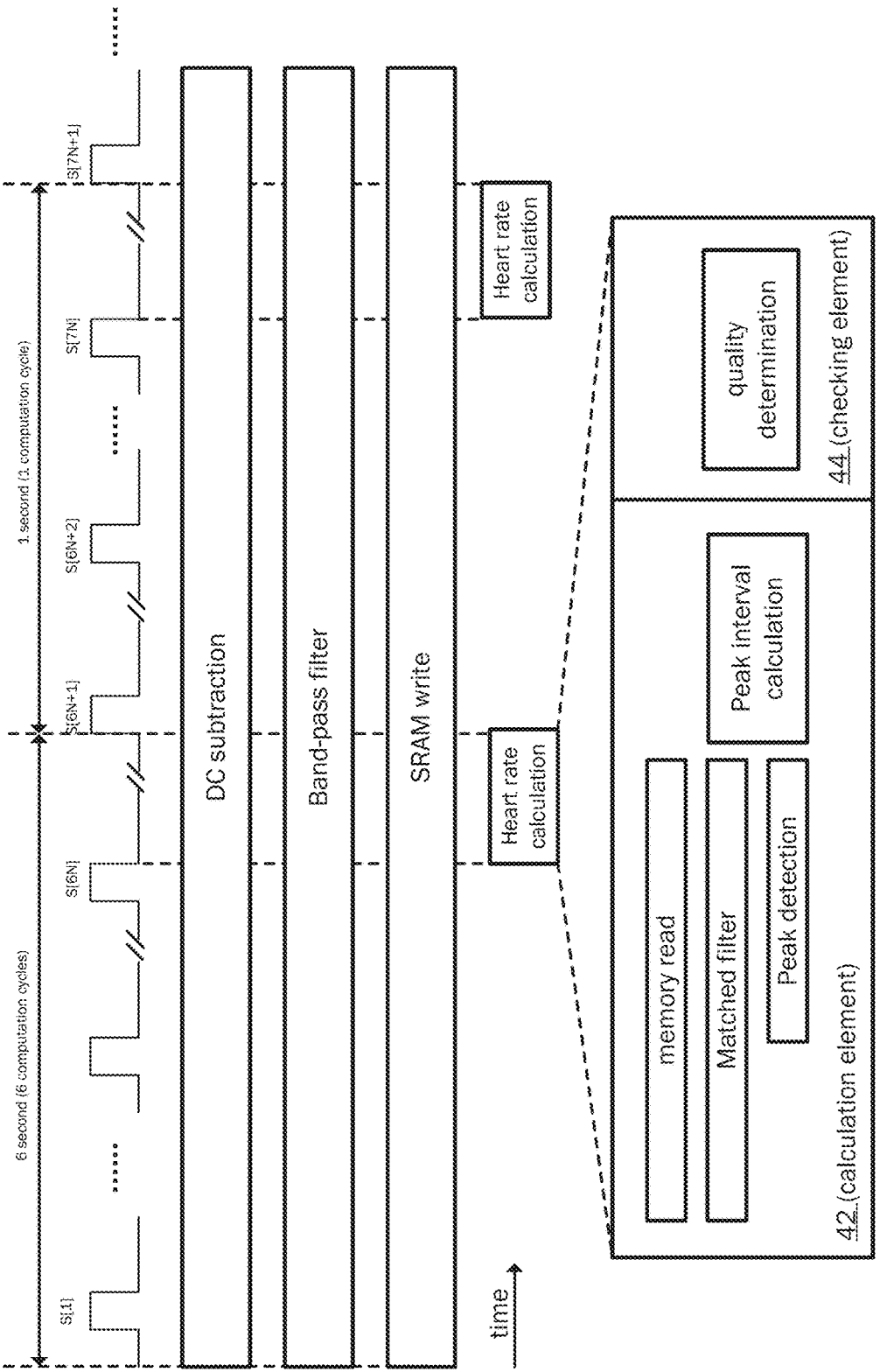
FIG. 4B illustrates a timing sequence of the heart rate calculation of the first calculator in accordance with another embodiment of the present disclosure.

FIG. 4A illustrates a timing sequence of the heart rate calculation of the first calculator 410, when the quality index is represented as the Q checking factor to transmit to the checking element 44 for validity indicator determination. FIG. 4B illustrates a timing sequence of the heart rate calculation of the first calculator 410, when PPG signal, filtered PPG signal, and/or PPG signal interval are represented as Q checking factors to transmit to the checking element 44 for validity indicator determination. Each heart rate calculation is performed after one computation cycle of the PPG signal, and one computation cycle has N samples. N is an integer, for example, N=50, 100, 150, and one computation cycle time can be 1 second. The first calculation requires multiple computation cycles to accumulate enough samples for matched filter processing, for example, the first calculation requires six (6) computation cycles or six (6) seconds. After the first calculation, the heart rate calculator can obtain an updated heart rate value every 1 computation cycle, for example, 1 second, for precise tracking.

FIG. 5A illustrates a method 500 of the heart rate calculation of the first calculator 410 in accordance with one embodiment of the present disclosure. Step S505 illustrates when the skin detector (e.g., skin detector 5 in FIG. 1) detects the presence of the object's skin, the optical sensing apparatus can obtain PPG signal from the light receiver (e.g., light receiver 2 in FIG. 1) to operate the heart rate calculation. Step S510 illustrates the calculation element of the first calculator of the heart rate calculator (e.g., calculation element 42 of the first calculator 410 in FIGS. 2A-2B) is configured to determine a first heart rate value according to the PPG signal. Furthermore, the calculation element can also be configured to store the PPG signal in the memory for other circuits or processor access for other applications. Step S515 illustrates the calculation element of the first calculator of the heart rate calculator can be configured to determine at least one quality checking factor to the checking element of the first calculator of the heart rate calculator. Step 520 illustrates the checking element of the first calculator of the heart rate calculator can be configured to determine a validity indicator based on at least one quality checking factor. Step S525 illustrates the first calculator of the heart rate calculator can determine whether to output the first heart rate value based on the validity indicator. Furthermore, the first calculator of the heart rate calculator can be chosen to output the PPG value based on the validity indicator.

FIG. 5B illustrates steps S515 to S525 of the heart rate calculation of the first calculator in accordance with another embodiment of the present disclosure. When at least one checking factor includes the quality index as shown in FIG. 3A, the calculation element of the first calculator can include a matched filter for generating a quality index according to the PPG signal. The matched filter can process the PPG signal to obtain a mean absolute value as the quality index. After step 515, step 521 illustrates the checking element of the first calculator can be configured to provide a validity indicator based on a comparison between the quality index and a reference index. Then, step 525 illustrates the first calculator can determine whether to output the first heart rate value based on the validity indicator.

FIG. 5C illustrates steps S515 to S525 of the heart rate calculation of the first calculator in accordance with another embodiment of the present disclosure. When at least one checking factor includes PPG signal, filtered PPG signal, and first heart rate value as shown in FIG. 3B. After step 515, step 523 illustrates the checking element of the first calculator can be configured to provide a validity indicator based on an evaluation of several indexes which is obtained from the PPG signal, filtered PPG signal, and PPG signal interval. Then, step 525 illustrates the first calculator can determine whether to output the first heart rate value based on the validity indicator.

Figure 6A:
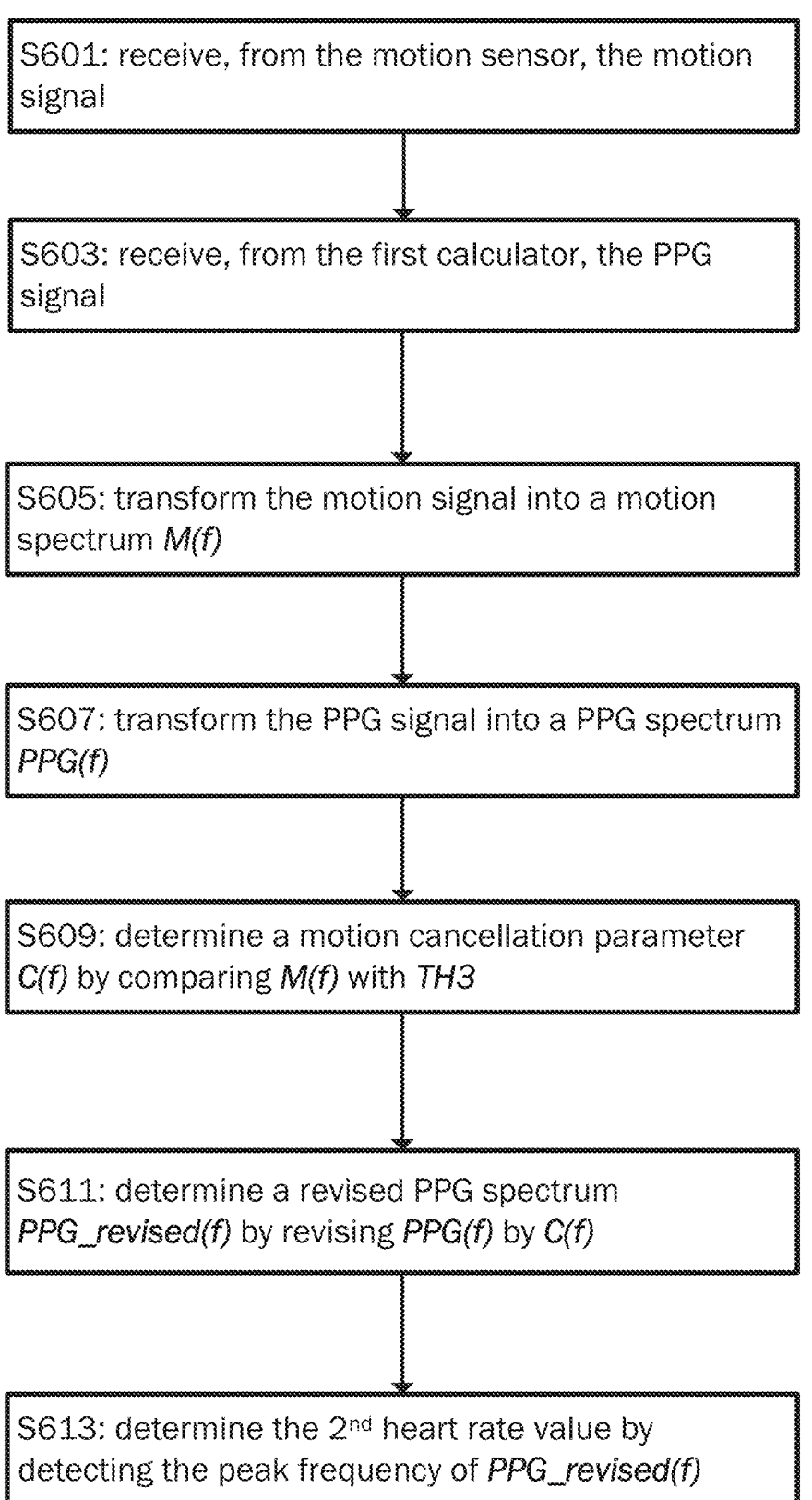
FIG. 6A illustrates a calculation flow of the second calculator of the heart rate calculator in accordance with one embodiment of the present disclosure.

FIG. 6A illustrates a calculation flow of the second calculator 420 in accordance with one embodiment of the present disclosure. FIG. 6B illustrates signal spectrum diagrams processed in the second calculator in accordance with one embodiment of the present disclosure. In step S601, the second calculator may receive the motion signal from the motion sensor, which is a time-varying signal. In step S603, the second calculator receives the PPG signal from the first calculator, which is a time-varying signal. In step S605, the second calculator transforms the time-varying motion signal into a motion spectrum M(f). The first spectrum diagram in FIG. 6B shows an illustrative example of motion spectrum. In step S607, the second calculator transforms the time-varying PPG signal into a PPG spectrum PPG(f). The third spectrum diagram in FIG. 6B shows an illustrative example of PPG spectrum. In step S609, the second calculator determines a motion cancellation parameter C(f) by comparing the motion spectrum M(f) with a predetermined threshold TH3. The first spectrum diagram in FIG. 6B shows an illustrative example of a predetermined threshold TH3 represented in a dotted line. The second spectrum diagram in FIG. 6B shows an illustrative example of motion cancellation parameter C(f). Referring to the first and second diagrams in FIG. 6, when M(f)≥TH3, it means there is movement interference from users on this frequency, then C(f) can be set to a first value (e.g., 0). When M(f)<TH3, it means there is no movement interference from users on this frequency, then C(f) can be set to a second value (e.g., 1). The second calculator generates C(f) based on this comparison, which can be used to eliminate movement interference on the PPG signal.

In one embodiment, when the motion sensor is implemented by an optical detector, the optical motion signal may include the PPG signal with heart rate information. In order to avoid regarding the heart rate information as a motion interference signal and eliminating it, the second calculator can set the motion cancellation parameter C(f) to the second value (e.g., 1) at a specific frequency within the estimated heart rate range to ensure that the heart rate information within the estimated heart rate range is not eliminated. So, the second calculator can obtain the heart rate information within the estimated heart rate range.

In step S611, the second calculator determines a revised PPG spectrum PPG_revised(f) by revising PPG(f) by C(f). In an embodiment, PPG_revised(f)=PPG(f)×C(f). The fourth spectrum diagram in FIG. 6B shows an illustrative example of revised PPG spectrum PPG_revised(f). PPG(f) in the third diagram compares with M(f) in the first diagram. PPG(f) has some interference signals similar to M(f), which are interference caused by movement. Referring to the fourth diagram, PPG(f) is revised by C(f) to obtain PPG_revised(f), which greatly reduces the interference signal as M(f), thereby the second calculator can obtain a more accurate heart rate value. In step S613, the second calculator determines a second heart rate value by detecting the peak frequency of PPG_revised(f).

Figure 7A:
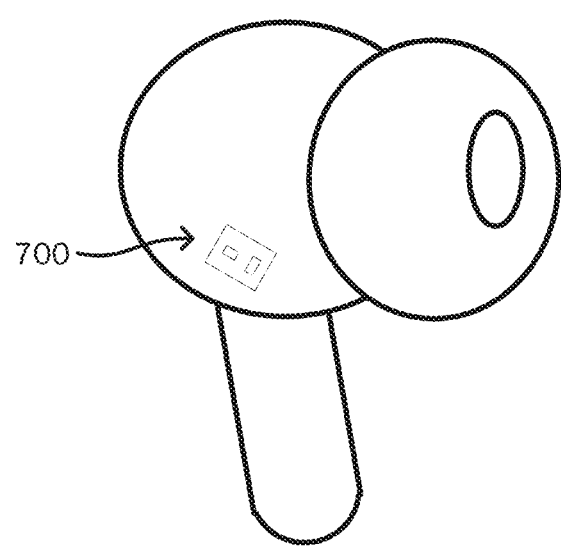
FIG. 7A shows an earbud including an optical sensing apparatus in accordance with one embodiment of the present disclosure.
Figure 7B:
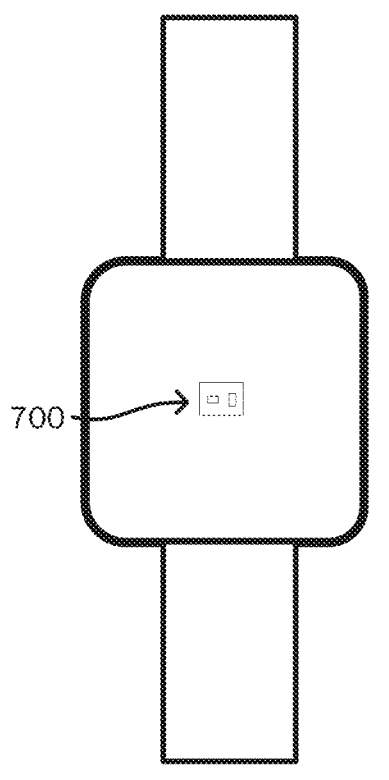
FIG. 7B shows a watch including an optical sensing apparatus in accordance with one embodiment of the present disclosure.
Figure 7C:
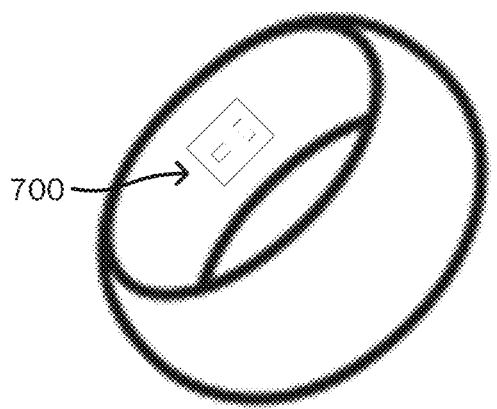
FIG. 7C shows a ring including an optical sensing apparatus in accordance with one embodiment of the present disclosure.

FIGS. 7A-7C show different wearable devices including the optical sensing apparatus in accordance with different embodiments of the present disclosure. FIG. 7A shows an earbud including an optical sensing apparatus 700. When the user wears the earbud to listen to music or communicate, the optical sensing apparatus 700 contacts the skin of the user and can be configured to measure various bioinformation at the same time. FIG. 7B shows a watch including at least one optical sensing apparatus 700. When the user wears the watch, the optical sensing apparatus 700 contacts the skin of the user and can be configured to measure various bioinformation. FIG. 7C shows a ring including at least one optical sensing apparatus 700. When the user wears the ring, the optical sensing apparatus 700 contacts the finger of the user and can be configured to measure various bioinformation. The optical sensing apparatus 700 can be one of the aforementioned optical sensing apparatuses. FIGS. 7A-7C show three examples of wearable devices, however suitable wearable devices such as helmet, wristband, glasses, can be installed the optical sensing apparatus to measure various bioinformation.

Figure 8:
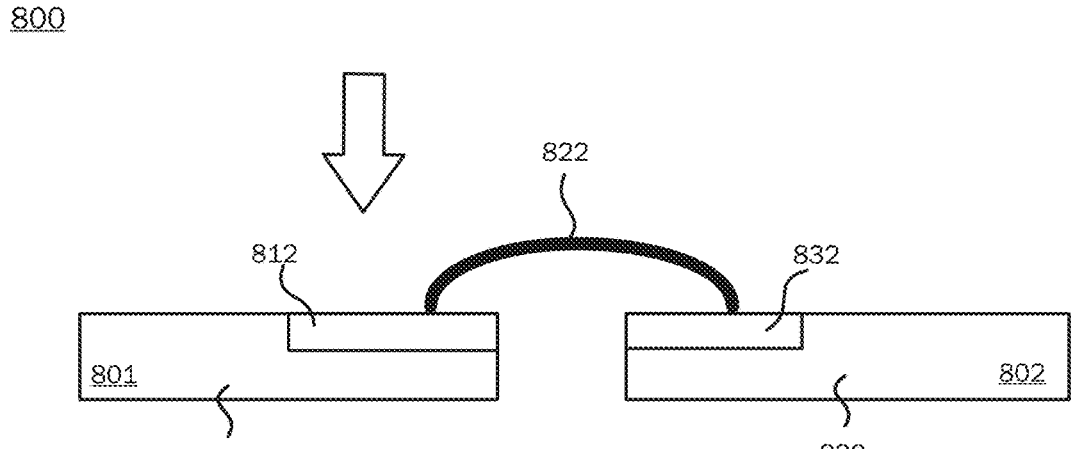
FIG. 8 illustrates an optical sensing apparatus in accordance with one embodiment of the present disclosure.

FIG. 8 illustrates an optical sensing apparatus 800 in accordance with one embodiment of the present disclosure. The optical sensing apparatus 800 includes a photodetector 801 and a control device 802 (e.g., CMOS circuitry) electrically coupled to the photodetector 801. The control device 802 can include the processor 10 as shown in FIG. 1. The photodetector 801 includes a first substrate 810 and a sensing area 812 deposited on the first substrate 810. The control device 802 includes a second substrate 830 and a circuitry area 832 (e.g., CMOS circuitry) carried by the second substrate 830. In an embodiment, the first substrate 810 and the second substrate 830 include the same material, for example, silicon substrate. In an embodiment, the photodetector 801 and the control device 802 can be disposed on a same plane of a circuit board (not shown), and the photodetector 801 is electrically coupled to the control device 802 via wire(s) 822 (e.g., wire-bonded). In another embodiment, in order to shrink the size of the optical sensing apparatus 800, the photodetector 801 can be stacked on the control device 802 and electrically coupled to the control device 802 via wire(s) or conductive glue. The sensing area 812 includes a material that can be different from (e.g., fabricated from a heterogeneous material) or the same as (e.g., fabricated from a homogeneous material) the first substrate 810. In one embodiment, the material of the sensing area 812 can include III-V material, such as P, N, Ga, In, Al. In another embodiment, the material of the sensing area 812 can include IV material such as Ge, Si.

Figure 9:
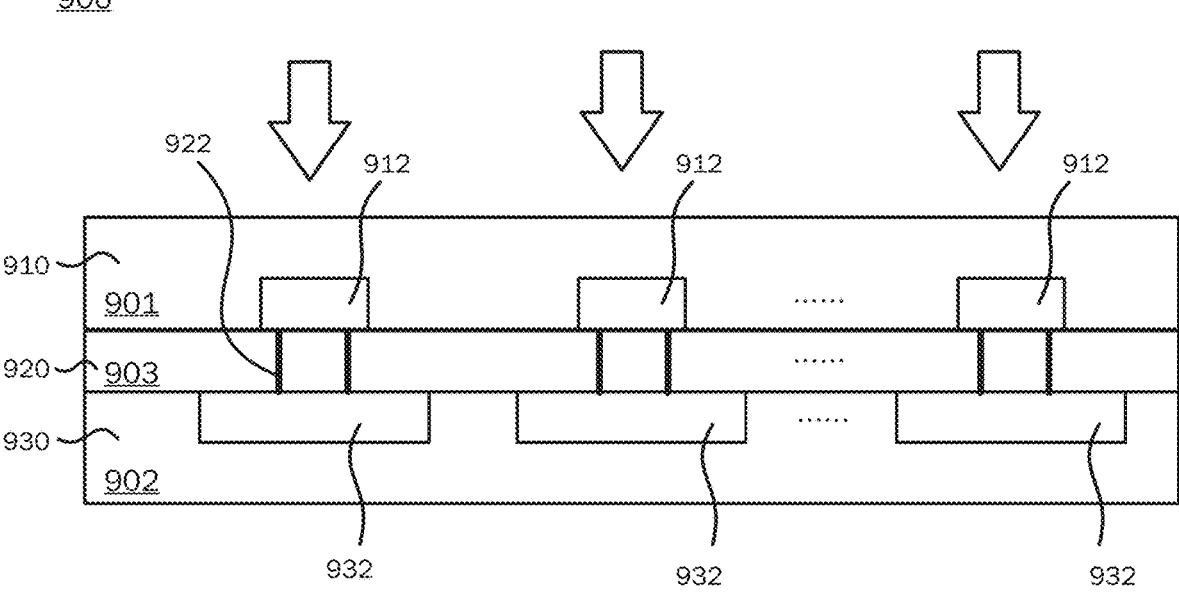
FIG. 9 illustrates an optical sensing apparatus in accordance with another embodiment of the present disclosure.

FIG. 9 illustrates an optical sensing apparatus 900 in accordance with another embodiment of the present disclosure. The optical sensing apparatus 900 includes a photodetector 901, a control device 902, and a bonding interface 903. The control device 902 can include the processor 10 as shown in FIG. 1. The photodetector 901 and the control device 902 are wafer-bonded via a bonding interface 903 (e.g., oxide or any other suitable materials). The photodetector 901 includes a first substrate 910 and a plurality of sensing areas 912 deposited on the first substrate 910. The control device 902 includes a second substrate 930 and a plurality of corresponding circuitry areas 932 carried by the second substrate 930. Each circuitry area 932 is electrically coupled to the corresponding sensing area 912 through the conductive route 922 of the bonding interface 903. The first substrate 710 and the second substrate 930 can both be silicon substrate. The sensing area 912 includes a material that can be different from (e.g., fabricated from a heterogeneous material) or the same as (e.g., fabricated from a homogeneous material) the first substrate 910. In one embodiment, the material of the sensing area 912 can include III-V material, such as P, N, Ga, In, Al. In another embodiment, the material of the sensing area 912 can include IV material such as Ge, Si.

While the disclosure has been described by way of example and in terms of a preferred embodiment, it is to be understood that the disclosure is not limited thereto. On the contrary, it is intended to cover various modifications and similar arrangements and procedures, and the scope of the appended claims therefore should be accorded to the broadest interpretation so as to encompass all such modifications and similar arrangements and procedures.

What is claimed is:

1. A method for obtaining a user heart rate value by an optical sensing apparatus, the method comprising:
    receiving, by a first calculator in a processor and from a light receiver, a PPG signal;
    receiving, by a second calculator in the processor and from a motion sensor, a motion signal;
    determining, by the first calculator in the processor, a first heart rate value according to the PPG signal without the motion signal;

determining, by the first calculator in the processor, a validity indicator according to the PPG signal, wherein the validity indicator represents a signal quality of the PPG signal;

determining, by a second calculator in the processor, a second heart rate value according to the PPG signal and the motion signal;

selecting, by a multiplexer in the processor and based on the validity indicator, the first heart rate value or the second heart rate value as the user heart rate value for output; and outputting, by the processor, the first heart rate value or the second heart rate value selected by the multiplexer.

2. The method of claim 1, wherein the determining step of the second heart rate value by the second calculator comprises:

receiving, by the second calculator and from the first calculator, the PPG signal;

transforming, by the second calculator, the motion signal into a motion spectrum;

transforming, by the second calculator, the PPG signal into a PPG spectrum;

determining, by the second calculator, a motion cancellation parameter by comparing the motion spectrum with a predetermined threshold;

determining, by the second calculator, a revised PPG spectrum by revising the PPG spectrum by the motion cancellation parameter; and determining, by the second calculator, the second heart rate value by detecting a peak frequency of the revised PPG spectrum.

3. The method of claim 2, wherein the determining step of the motion cancellation parameter comprises:

when the motion spectrum at a first frequency is not less than the predetermined threshold, the motion cancellation parameter is a first value at the first frequency; and when the motion spectrum at a second frequency is less than the predetermined threshold, the motion cancellation parameter is a second value at the second frequency.

4. The method of claim 3, wherein the first value is 0 and the second value is 1.

5. The method of claim 3, further comprising setting the motion cancellation parameter to the second value at a specific frequency within an estimated heart rate range.

6. The method of claim 2, wherein the revised PPG spectrum is derived by multiplying the PPG spectrum by the motion cancellation parameter.

7. The method of claim 1, wherein the motion sensor is implemented by an optical detector operating at a different wavelength than the light receiver.

8. The method of claim 7, further comprising:

receiving, by the first calculator in the processor and from the motion sensor, the motion signal; and determining, by the first calculator in the processor, a validity indicator according to analysis of the PPG signal and analysis of the motion signal.

9. The method of claim 1, further comprising:

receiving, by a PPG evaluator in a processor and from a light receiver, the PPG signal;

classifying, by the PPG evaluator in the processor, the PPG signal and determining a classification information; and outputting, by the PPG evaluator in the processor, an evaluation result based on the classification information.

10. The method of claim 1, wherein the light receiver and the motion sensor are implemented by a single light receiver.

11. An optical sensing apparatus configured to obtain a user heart rate value, comprising:

a motion sensor;

a light receiver; and a processor comprising a first calculator and a second calculator, the processor being configured to:

receive, by the first calculator and from the light receiver, a PPG signal;

receive, by the second calculator and from the motion sensor, a motion signal;

determine, by the first calculator, a first heart rate value according to the PPG signal and without the motion signal;

determine, by the first calculator, a validity indicator according to the PPG signal, wherein the validity indicator represents a signal quality of the PPG signal;

determine, by the second calculator, a second heart rate value according to the PPG signal and the motion signal;

select, by a multiplexer in the processor and based on the validity indicator, the first heart rate value or the second heart rate value as the user heart rate value for output; and output the first heart rate value or the second heart rate value selected by the multiplexer.

12. The optical sensing apparatus of claim 11, wherein the motion sensor is implemented by an optical detector operating at a different wavelength than the light receiver.

13. The optical sensing apparatus of claim 11, wherein the light receiver and the motion sensor are implemented by a single light receiver.

14. The optical sensing apparatus of claim 11, wherein the second calculator is configured to:

receive, from the first calculator, the PPG signal;

transform, the motion signal into a motion spectrum;

transform, the PPG signal into a PPG spectrum;

determine, a motion cancellation parameter by comparing the motion spectrum with a predetermined threshold;

determine, a revised PPG spectrum by revising the PPG spectrum by the motion cancellation parameter; and determine, the second heart rate value by detecting a peak frequency of the revised PPG spectrum.

15. The optical sensing apparatus of claim 14, wherein when the motion spectrum at a first frequency is not less than the predetermined threshold, the motion cancellation parameter is a first value at the first frequency; and when the motion spectrum at a second frequency is less than the predetermined threshold, the motion cancellation parameter is a second value at the second frequency.

16. The optical sensing apparatus of claim 14, wherein the revised PPG spectrum is derived by multiplying the PPG spectrum by the motion cancellation parameter.

17. The method of claim 1, wherein the first calculator comprises a band-pass filter circuit, a matched filter circuit, and an analysis circuit, and wherein determining the validity indicator comprises:

calculating, using the band-pass filter circuit and based on the PPG signal, a filtered PPG signal having a higher signal-to-noise ratio than the PPG signal;

calculating, using the matched filter circuit and based on the PPG signal, a quality index representing a moving average associated with the PPG signal;

calculating, using the analysis circuit and based on the PPG signal, a PPG signal interval representing an interval of peaks of the PPG signal; and determining the validity indicator based on at least one of the filtered PPG signal, the quality index, the PPG signal, and the PPG signal interval.

18. The method of claim 17, wherein the first calculator comprises a stability detector, a signal strength detector, a noise floor detector, a periodicity detector, and a decision logic circuit, and wherein determining the validity indicator comprises:

calculating, using the stability detector and based on the PPG signal, a stability index representing a stability of the PPG signal;

calculating, using the signal strength detector and based on the filtered PPG signal, a signal strength index representing a signal strength of the PPG signal;

calculating, using the noise floor detector and based on the filtered PPG signal, a noise floor index representing a noise floor of the PPG signal;

calculating, using the periodicity detector and based on the filtered PPG signal and the PPG signal interval, a periodicity index representing a periodicity of the PPG signal; and determining, using the decision logic circuit, the validity indicator based on at least one of the stability index, the signal strength index, the noise floor index, and the periodicity index.

19. The optical sensing apparatus of claim 11, wherein the first calculator comprises a band-pass filter circuit, a matched filter circuit, and an analysis circuit, and wherein determining the validity indicator comprises:

calculating, using the band-pass filter circuit and based on the PPG signal, a filtered PPG signal having a higher signal-to-noise ratio than the PPG signal;

calculating, using the matched filter circuit and based on the PPG signal, a quality index representing a moving average associated with the PPG signal;

calculating, using the analysis circuit and based on the PPG signal, a PPG signal interval representing an interval of peaks of the PPG signal; and determining the validity indicator based on at least one of the filtered PPG signal, the quality index, the PPG signal, and the PPG signal interval.

20. The optical sensing apparatus of claim 19, wherein the first calculator comprises a stability detector, a signal strength detector, a noise floor detector, a periodicity detector, and a decision logic circuit, and wherein determining the validity indicator comprises:

calculating, using the stability detector and based on the PPG signal, a stability index representing a stability of the PPG signal;

calculating, using the signal strength detector and based on the filtered PPG signal, a signal strength index representing a signal strength of the PPG signal;

calculating, using the noise floor detector and based on the filtered PPG signal, a noise floor index representing a noise floor of the PPG signal;

calculating, using the periodicity detector and based on the filtered PPG signal and the PPG signal interval, a periodicity index representing a periodicity of the PPG signal; and determining, using the decision logic circuit, the validity indicator based on at least one of the stability index, the signal strength index, the noise floor index, and the periodicity index.

\* \* \* \* \*